(12) United States Patent
June

(10) Patent No.: US 6,632,789 B1
(45) Date of Patent: Oct. 14, 2003

(54) METHODS FOR MODULATING T CELL RESPONSES BY MANIPULATING INTRACELLULAR SIGNAL TRANSDUCTION

(75) Inventor: Carl H. June, Rockville, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 08/245,282

(22) Filed: Apr. 29, 1994

(51) Int. Cl.$^7$ .................... A01N 61/00; A01N 43/16; A61K 39/395; A61K 45/00
(52) U.S. Cl. .................... 514/1; 514/453; 424/130.1; 424/278.1
(58) Field of Search .................... 435/240.2, 240.1, 435/244; 424/278.1, 130.1; 514/453, 1

(56) References Cited

U.S. PATENT DOCUMENTS 5,504,103 A * 4/1996 Bonjouklian et al. ....... 514/453

FOREIGN PATENT DOCUMENTS

WO    WO 90/05541    5/1990

OTHER PUBLICATIONS

Ward et al EJD 23: 2572, 1993.*
Vondenhergle et al JEM 175: 951, 1992.*
Obada et al JBC 269(5): 3563, 1994.*
Ward et al EJI 22: 45, 1992.*
Abe, R. et al., "T Cell Receptor–mediated Recognition of Self–Ligand Induces Signaling in Immature Thymocytes before Negative Selection" *J. Exp. Med.,* vol. 176, pp. 459–468, Aug. 1992.
Baggiolini, M. et al., "Inhibition of the Phagocytosis–Induced Respiratory Burst by the Fungal Metabolite Wortmannin and Some Analogues" *Experimental Cell Research,* vol. 169, pp. 408–418, 1987.
Blunden, G. et al., "Mycotoxins in food" *Medical Laboratory Sciences,* vol. 48, pp. 271–282, 1991.
Closse, A. et al., "2,3–Dihydrobenzofuran–2–ones: A New Class of Highly Potent Antiinflammatory Agents" *J. Med. Chem.,* vol. 24, pp. 1465–1471, 1981.
Gunther, R. et al., "Acute Pathological Effects on Rats of Orally Administered Wortmannin–Containing Preparations and Purified Wortmannin from *Fusarium Oxysporum*" *Fd. Chem. Toxic.,* vol. 27, No. 3, pp. 173–179, 1989.
Gunther, R. et al., "Immuosuppressive Effects of Dietary Wortmannin on Rats and Mice" *Immunopharmacology and Immunotoxicology,* vol. 11, No. 4, pp. 559–570, 1989.
Harding, F.K. et al., "CD28–mediated signalling co–stimulates murine T cells and prevents induction of anergy in T–cell clones" *Nature,* vol. 356, pp. 607–609, Apr. 16, 1992.
June, C.H., "Signal transduction in T cells" *Current Opinion in Immunology,* vol. 3, pp. 287–293, 1991.

June, C.H. et al., "Evidence for the Involvement of Three Distinct Signals in the Induction of IL–2 Gene Expression in Human T Lymphocytes" *J. Immunol.,* vol. 143, No. 1, pp. 153–161, Jul. 1, 1989.
June, C.H. et al., "Role of the CD28 receptor in T–cell activation" *Immunology Today,* vol. 11, No. 6, pp. 211–216, 1990.
Ledbetter, J.A. et al., "CD28 Ligation in T–Cell Activation: Evidence for Two Signal Transduction Pathways" *Blood,* vol. 75, No. 1, pp. 1531–1539, Apr. 1, 1990.
Ledbetter, J.A. et al., "Crosslinking of surface antigens cause mobilization of intracellular ionized calcium in T lymphocytes" *Proc. Natl. Acad. Sci. USA,* vol. 84, pp. 1384–1388, Mar. 1987.
Lee, K. et al., "The CD28 Signal Transduction Pathway in T Cell Activation" in *Advances of Cell Regulation of Cell Growth, vol. 2—Cell Activation: Genetic Approaches,* J.J. Mond et al. (eds.), New York: Raven Press, Ltd., pp. 141–160, 1991.
Ley, S.C. et al., "The T cell receptor/CD3 complex and CD2 stimulate the tyrosine phosphorylation of indistinguishable patterns of polypeptides in the human T leukemic cell line Jurkat" *Eur. J. Immunol.,* vol. 21, pp. 2203–2209, 1991.
Lu, Yiling et al., "CD28–Induced T Cell Activation: Evidence for a Protein–Tyrosine Kinase Signal Transduction Pathway" *J. Immunol.* vol. 149, No. 1, pp. 24–29, Jul. 1, 1992.

(List continued on next page.)

*Primary Examiner*—Anne M. Wehbé
(74) *Attorney, Agent, or Firm*—Lahive & Cockfield, LLP; Amy E. Mandragouras, Esq.; DeAnn F. Smith, Esq.

(57) ABSTRACT

Methods for modulating T cell responses by manipulating intracellular signals associated with T cell costimulation are disclosed. The methods involve inhibiting or stimulating the production of at least one D3-phosphoinositide in a T cell. Production of D3-phosphoinositides can be manipulated by contacting a T cell with an inhibitor or activator of phosphatidylinositol 3-kinase. Inhibitors of phosphatidylinositol 3-kinase for use in the methods of the invention include wortmannin and quercetin, or derivatives or analogues thereof. The methods of the invention can further comprise modulating other intracellular signals associated with costimulation, such as protein tyrosine phosphorylation, for example by modulating the activity of a protein tyrosine kinase or a protein tyrosine phosphatase in the T cell. Inhibition of a T cell response in accordance with the disclosed methods is useful therapeutically in situations where it is desirable to inhibit an immune response to an antigen(s), for example in organ or bone marrow transplantation and autoimmune diseases. Alternatively, stimulation of a T cell response in accordance with the disclosed methods is useful therapeutically to enhance an immune response to an antigen(s), for example to stimulate an anti-tumor response in a subject with a tumor, to stimulate a response against a pathogenic agent or increase the efficacy of vaccination. Novel screening assays for identifying inhibitors or activators of phosphatidylinositol 3-kinase, which can be used to inhibit or stimulate a T cell response, are also disclosed.

19 Claims, 8 Drawing Sheets

OTHER PUBLICATIONS

Nunes. J. et al., "SIgnaling through CD28 T–cell activation pathway involves an inositol phospholipid–specific phospholipase C activity" *Biochem. J.*, vol. 293, pp. 835–842, 1993.

Okada, T. et al., "Blockage of Chemotactic Peptide–induced Stimulation of Neutrophils by Wortmannin as a Result of Selective Inhibition of Phosphatidylinositol 3–Kinase" *J. Biol. Chem.*, vol. 269, No. 5, pp. 3562–3567, Feb. 4, 1994.

Okada, T. et al., "Essential Role of Phosphatidylinositol 3–Kinase in Insulin–induced Glucose Transport and Antilipolysis in Rat Adipocytes" *J. Biol. Chem.*, vol. 269, No. 5, pp. 3568–3573, Feb. 4, 1994.

O'Shea, J.J. et al., "Activation of human peripheral blood T lymphocytes by pharmacological induction of protein–tyrosine phosphorylation" *Proc. Natl. Acad. Sci. USA*, vol. 89, pp. 10306–10310, Nov. 1992.

Pérez–Blas, M. et al., "Impaired T cell signal transduction through CD28 in a patient with idiopathic thrombocytopenia" *Clin. Exp. Immunol.*, vol. 85, pp. 424–428, 1991.

Prasad, K.V.S., et al., "Phosphatidylinositol (PI) 3–Kinase to PI 4–Kinase Binding to the CD4–p56$^{lck}$ Complex: the p56$^{lck}$ SH3 Domain Binds to PI 3–Kinase but Not Pi 4–Kinase" *Molecular and Cellular Biology*, vol. 13, No. 12, pp. 7708–7717, Dec. 1993.

Prasad, K.V.S., et al., "Src–homology 3 domain of protein kinase p59$^{fyn}$ mediates binding phosphatidylinositol 3–kinase in T cells" *Proc. Natl. Acad. Sci. USA*, vol. 90, pp. 7366–7370, Aug. 1993.

Schwartz, R.H., "A Cell Culture Model for T Lymphocyte Clonal Anergy" *Science*, vol. 248, pp. 1349–1356, Jun. 15, 1990.

Thompson, P.A. et al., "Identification of distinct populations of PI–3 kinase activity following T–cell activation" *Oncogene*, vol. 7, pp. 719–725, 1992.

Truitt, K.E. et al., "Stimulation of CD28 Triggers an Association between CD28 and Phosphatidylinositol 3–Kinase in Jurkat T Cells" *J. Exp. Med.*, vol. 179, pp. 1071–1076, Mar. 1994.

Vandenberghe, P. et al., "Antibody and B7/BB1–mediated Ligation of the CD28 Receptor Induces Tyrosine Phosphorylation in Human T Cells" *J. Exp. Med.*, vol. 175, pp. 951–960, Apr. 1992.

Ward, S.G. et al., "Ligation of CD28 receptor by B7 induces formation of D–3 phosphoinositides in T lymphocytes independently of T cell receptor/CD3 activation" *Eur. J. Immunol.*, vol. 23, pp. 2572–2577, 1993.

Ward, S.G. et al., "Regulation of D–3 phospholinositides during T cell activation via the T cell antigen receptor/CD3 complex and CD2 antigens" *Eur. J. Immunol.*, vol. 22, pp. 45–49, 1992.

Ward, S.G. et al., "Regulation of Phosphoinositide Kinases in T Cells" *J. Biol. Chem.*, vol. 267, No. 33, pp. 23862–23869, Nov. 25, 1992.

Wiesinger, D. et al., Antiinflammatory Activity of the New Mould Metabolite 11–Desacetoxy–Wortmannin and Some of its Derivatives *Experientia*, vol. 30, pp. 135–136, 1974.

Wu, W. and C.J. Mirocha, "Decreased Immunological Responses by Wortmannin–Containing Rice Culture and *Fusarium Oxysporium* and by Purified Wortmannin in Avian Species" *Immunopharmacology and Immunotoxicology*, vol. 14, No. 4, pp. 913–923, 1992.

Yang, S.Y. et al., "A Novel Activation Pathway for Mature Thymocytes" *J. Exp. Med.*, vol. 168, pp. 1457–1468, Oct. 1988.

Yano, H. et al., "Inhibition of Histamine Secretion by Wortmannin through the Blockade of Phosphatidylinositol 3–Kinase in RBL–2H3 Cells" *J. Biol. Chem.*, vol. 268, No. 34, pp. 25846–25856, Dec. 5, 1993.

Schwartz, A., et al., "Quercetin Inhibition of the Induction and Fuction of Cytotoxic T Lymphocytes," *Immunopharmacology*, vol. 4, 125–138, (1982).

Wu, W. and Mirocha, C.J., "Wortmannin (A Mycotoxin) Inhibited Immune Responses in Chickens," *Poultry Science*, vol. 71, suppl. 1, 13, (1992).

Yoshida, M., et al., "Quercetin Arrests Human Leukemic T–Cells in Late $G_1$ Phase of the Cell Cycle," *Cancer Research*, vol. 52, 6676–6681, (1992).

Ward, Stephen G. et al. "Inhibition of CD28–mediated T cell costimulation by the phosphoinositide 3–kinase inhibitor wortmannin" *Eur. J. Immunol.* 25:526–532 (1995).

\* cited by examiner

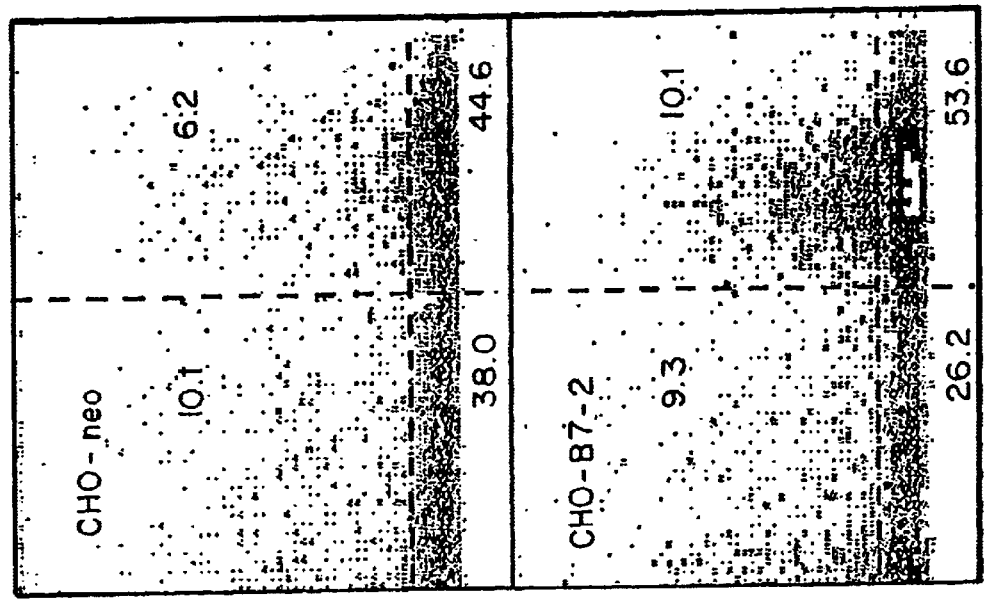
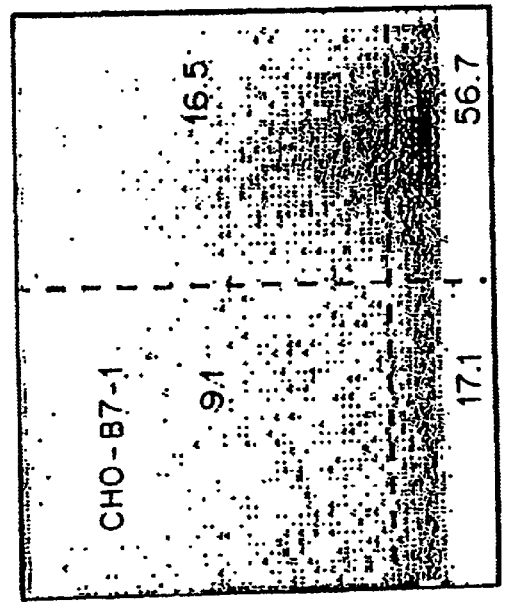
FIG. 5

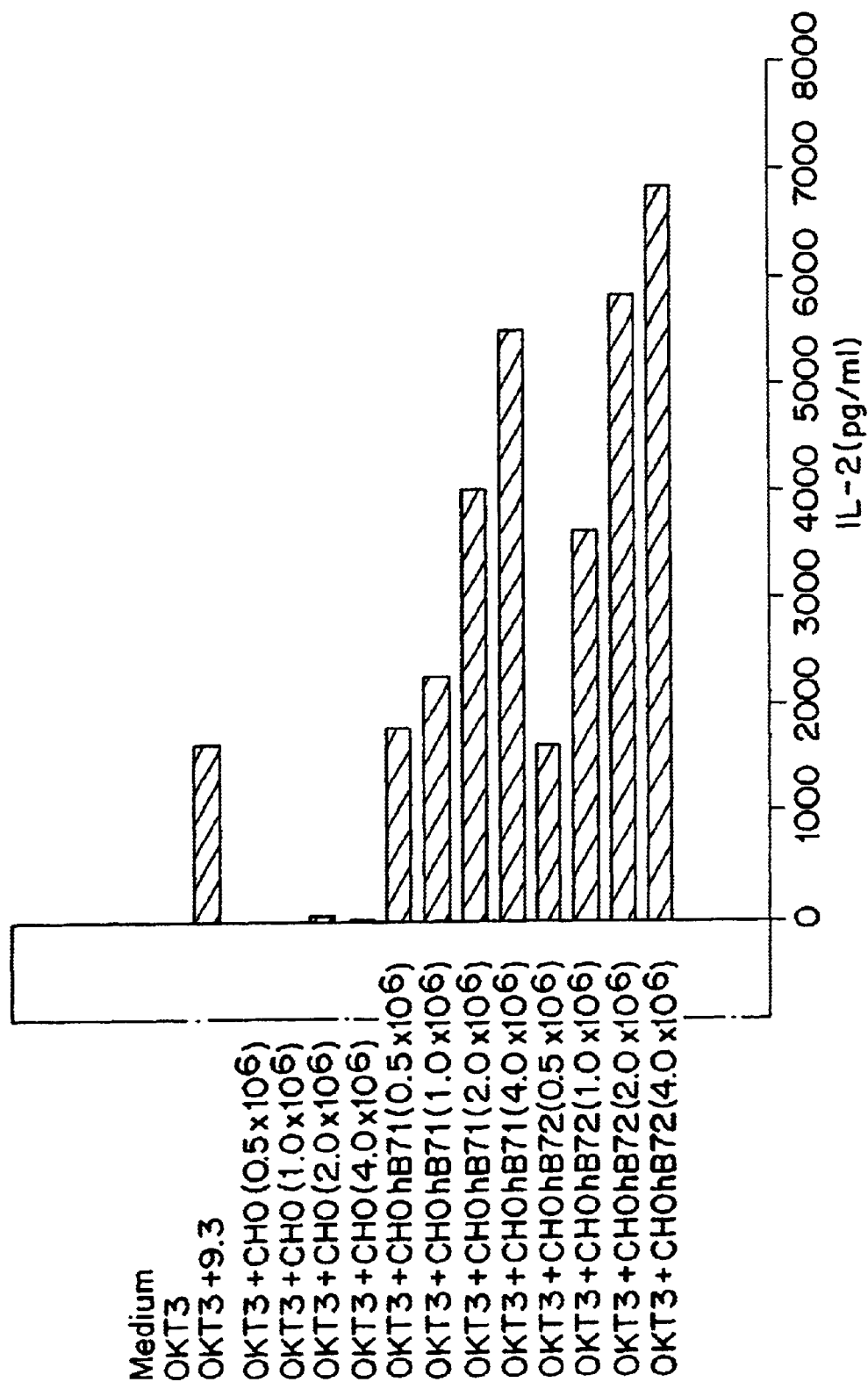

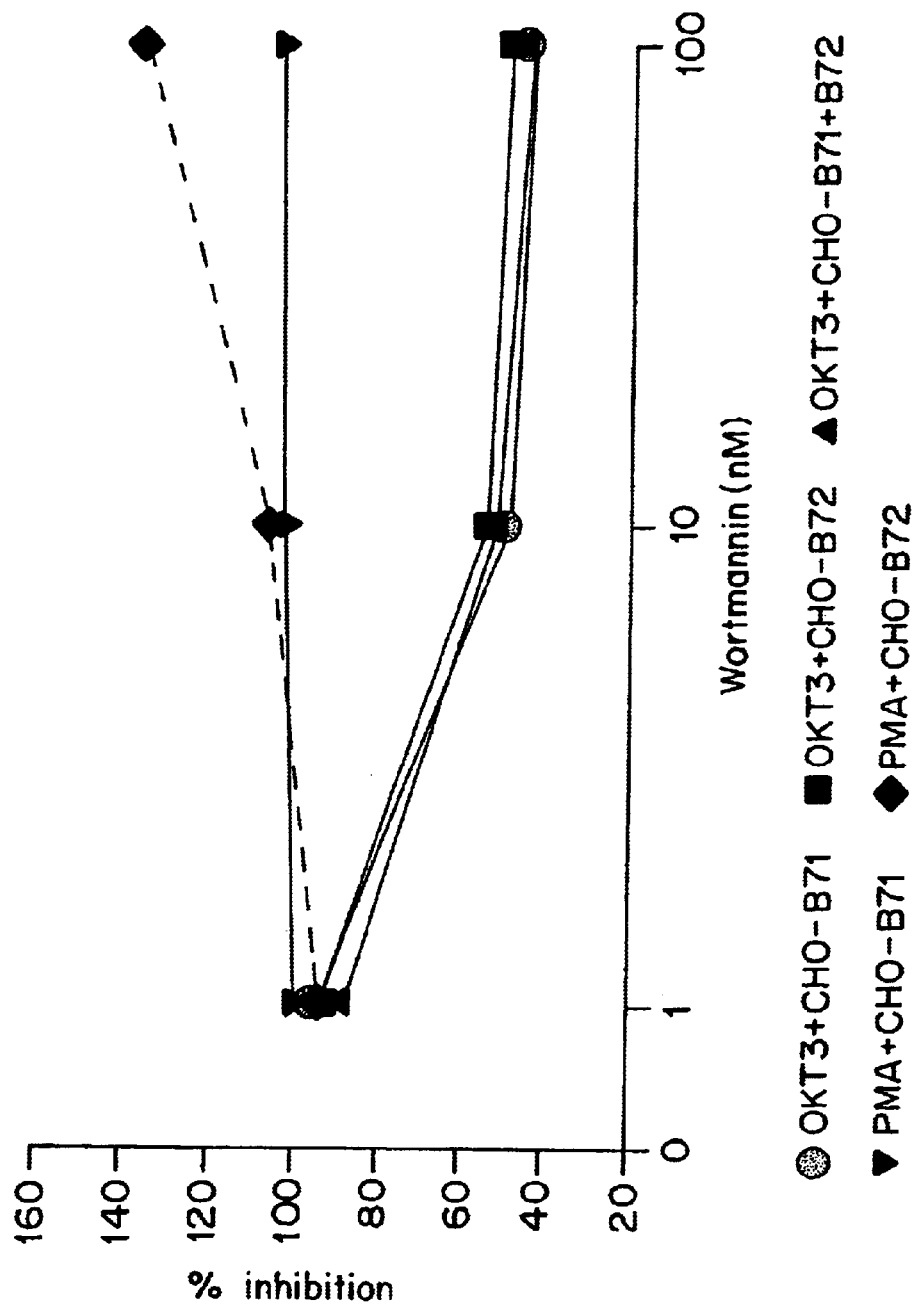

METHODS FOR MODULATING T CELL RESPONSES BY MANIPULATING INTRACELLULAR SIGNAL TRANSDUCTION

BACKGROUND OF THE INVENTION

The induction of antigen-specific T cell responses involves multiple interactions between cell surface receptors on T cells and ligands on antigen presenting cells (APCs). The primary interaction is between the T cell receptor (TCR)/CD3 complex on a T cell and a major histocompatibility complex (MHC) molecule/antigenic peptide complex on an antigen presenting cell. This interaction triggers a primary, antigen-specific, activation signal in the T cell. In addition to the primary activation signal, induction of T cell responses requires a second, costimulatory signal. In the absence of proper costimulation, TCR signaling can induce a state of anergy in the T cell. Subsequent appropriate presentation of antigen to an anergic T cell fails to elicit a proper response (see Schwartz, R. H. (1990) *Science* 248:1349).

A costimulatory signal can be triggered in a T cell through a T cell surface receptor, such as CD28. For example, it has been demonstrated that suboptimal polyclonal stimulation of T cells (e.g. by anti-CD3 antibodies or phorbol ester, either of which can provide a primary activation signal) can be potentiated by crosslinking of CD28 with anti-CD28 antibodies (Linsley, P. S. et al. (1991) *J. Exp. Med.* 173:721; Gimmi, C. D. et al. (1991) *Proc. Natl. Acad. Sci. USA* 88:6575). Moreover, stimulation of CD28 can prevent the induction of anergy in T cell clones (Harding, F. A. (1992) *Nature* 356:607–609). Natural ligands for CD28 have been identified on APCs. CD28 ligands include members of the B7 family of proteins, such as B7-1(CD80) and B7-2 (B70) (Freedman, A. S. et al. (1987) *J. Immunol.* 137:3260–3267; Freeman, G. J. et al. (1989) *J. Immunol.* 143:2714–2722; Freeman, G. J. et al. (1991) *J. Exp. Med.* 174:625–631; Freeman, G. J. et al. (1993) *Science* 26:909–911; Azuma, M. et al. (1993) *Nature* 366:76–79; Freeman, G. J. et al. (1993) *J. Exp. Med.* 178:2185–2192). In addition to CD28, proteins of the B7 family have been shown to bind another surface receptor on T cells related to CD28, termed CTLA4, which may also play a role in T cell costimulation (Linsley, P. S. (1991) *J. Exp. Med.* 174:561–569; Freeman, G. J. et al. (1993) *Science* 262:909–911).

The elucidation of the receptor:ligand relationship of CD28/CTLA4 and the B7 family of proteins, and the role of this interaction in costimulation, has led to therapeutic approaches involving manipulation of the extracellular interactions of surface receptors on T cells which bind costimulatory molecules. For example, a CTLA4Ig fusion protein, which binds to both B7-1 and B7-2 and blocks their interaction with CD28/CTLA4, has been used to inhibit rejection of allogeneic and xenogeneic grafts (see e.g., Turka, L. A. et al. (1992) *Proc. Natl. Acad. Sci. USA* 89:11102–11105; Lenschow, D. J. et al. (1992) *Science* 257:789–792). Similarly, antibodies reactive with B7-1 and/or B7-2 have been used to inhibit T cell proliferation and IL-2 production in vitro and inhibit primary immune responses to antigen in vivo (Hathcock K. S. et al. (1993) *Science* 262:905–907; Azuma, M. et al. (1993) *Nature* 366:76–79; Powers, G. D. et al. (1994) *Cell. Immunol.* 153:298–311; Chen C. et al. (1994) *J. Immunol.* 152:2105–2114). Together, these studies indicate that T cell surface receptors which bind costimulatory molecules such as B7-1 and B7-2 are desirable targets for manipulating immune responses.

While the extracellular interactions between CD28/CTLA4 with their ligands have been characterized in some detail, little is known regarding the intracellular events that occur in a T cell following ligation of these molecules. T cell costimulation is thought to involve an intracellular signal transduction pathway distinct from signalling through the TCR since the costimulatory pathway is resistant to the inhibitory effects of cyclosporin A (see June, C. H. et al. (1990) *Immunology Today* 11:211–216) Protein tyrosine phosphorylation has been shown to occur in T cells upon CD28 ligation and it has been demonstrated that a protein tyrosine kinase inhibitor, herbimycin A, can inhibit CD28-induced IL-2 production (Vandenberghe, P. et al. (1992) *J. Exp. Med.* 175:951–960; Lu, Y. et al. (1992) *J. Immunol.* 149:24–29).

SUMMARY OF THE INVENTION

This invention relates to the regulation of T cell responses by manipulation of intracellular signal transduction. In particular, intracellulal signalling events which occur upon costimulation of a T cell are manipulated. The invention encompasses methods for inhibiting or stimulating T cell responses by inhibiting or stimulating one or more intracellular signals which result from ligation of a surface receptor on a T cell which binds a costimulatory molecule. It has now been discovered that CD28 receptor stimulation leads to the production of D3-phosphoinositides within a T cell. Moreover, it has been discovered that inhibition of the activity of phosphatidylinositol 3-kinase in a T cell can inhibit T cell responses, such as lymphokine production and cellular proliferation. These discoveries indicate a functional role for D3-phosphoinositides in a costimulatory signal transduction pathway and provide phosphatidylinositol 3-kinase as an intracellular target for modulation of T cell responses. Accordingly, intracellular signalling events involving D3-phosphoinositides can be modulated either to inhibit a costimulatory signal and thereby induce T cell unresponsiveness, or to trigger a costimulatory signal and thereby generate a T cell response. In addition, novel screening assays for identifying inhibitors or activators of phosphatidylinositol 3-kinase, which can be used to inhibit or stimulate a T cell response, are within the scope of the invention.

One aspect of the invention pertains to methods for inhibiting a response by a T cell which expresses a surface receptor that binds a costimulatory molecule. These methods involve contacting the T cell with an agent which inhibits production of D3-phosphoinositides in the T cell. In one embodiment, the agent is an inhibitor of a phosphatidylinositol 3-kinase, such as the fungal metabolite wortmannin or the bioflavenoid quercetin, or derivatives or analogues thereof (e.g. LY294002). In another embodiment of the method of the invention, the T cell is contacted with at least one additional agent which inhibits a different intracellular signal associated with costimulation, such as protein tyrosine phosphorylation. For example, the T cell can be contacted both with an inhibitor of phosphatidylinositol 3-kinase and with an inhibitor of a protein tyrosine kinase. A preferred inhibitor of a protein tyrosine kinase is herbimycin A. Alternatively, protein tyrosine phosphorylation can be inhibited in a T cell by a tyrosine phosphatase or an activator of a tyrosine phosphatase. In this embodiment, the T cell can be contacted with an inhibitor of phosphatidylinositol 3-kinase and with a molecule, e.g., an antibody, which binds to and activates a cellular tyrosine phosphatase, such as CD45 or Hcph.

The invention also provides methods for inducing unresponsiveness to an antigen in a T cell by triggering a primary, antigen-specific signal in a T cell while interfering with an intracellular signal associated with costimulation in the T cell. As a result of interfering with costimulatory signal transduction, the T cell fails to receive a proper costimulatory signal in the presence of the antigen and antigen-specific unresponsiveness is induced in the T cell. To induce T cell unresponsiveness, an antigen-specific T cell is contacted with the antigen in a form suitable for stimulation of a primary activation signal in the T cell, together with an agent which inhibits production of D-3 phosphoinositides in the T cell. For example, a T cell can be contacted with an antigen presented by an APC together with an inhibitor of phosphatidylinositol 3-kinase, such as wortmannin or quercetin or derivatives or analogues thereof (e.g. LY294002). Additionally, other intracellular signals associated with costimulation, such as protein tyrosine phosphorylation, can be inhibited in the T cell.

Methods for inhibiting T cell responses and for inducing T cell unresponsiveness are useful in situations where it is desirable to down-modulate an immune response, for example in a transplant recipient (e.g., of an organ graft or bone marrow graft etc.) or a subject suffering from an autoimmune disease or other disorder associated with an abnormal immune response. An agent which inhibits signal transduction associated with costimulation (e.g., an inhibitor of inositol phosphate 3-kinase) can be administered to a subject or, alternatively, T cells can be obtained from the subject, treated in vitro as described herein and administered to the subject.

Another aspect of the invention pertains to methods for stimulating a response by a T cell which has received a primary activation signal and expresses a surface receptor that binds a costimulatory molecule. These methods involve contacting the T cell with an agent which stimulates production of D-3 phosphoinositides in the T cell, such as an activator of phosphatidylinositol 3-kinase. In another embodiment, the T cell is contacted with an agent which stimulates production of D-3 phosphoinositides and at least one additional agent which stimulates a different intracellular signal associated with costimulation, such as protein tyrosine phosphorylation. For example, the T cell can be contacted with an activator of phosphatidylinositol 3-kinase together with an activator of a protein tyrosine kinase, such as pervanadate. Alternatively, an inhibitor of a cellular phosphatase, such as CD45 or Hcph, can be used in conjunction with a PI3K activator. In yet another embodiment of the invention, an antigen-specific T cell response is stimulated by contacting an antigen-specific T cell with the antigen together with an agent which stimulates production of D-3 phosphoinositides in the T cell, thereby stimulating both a primary activation signal and a costimulatory signal in the T cell.

Methods for stimulating T cell responses are useful in situations where it is desirable to up-regulate an immune response. For example a response against a tumor in a tumor-bearing subject can be stimulated or a response against a pathogen (e.g., a bacteria, a virus, such as HIV, fungus, parasite etc.) in a subject can be stimulated. Additionally, the methods can be used to enhance the efficacy of vaccination. An agent which stimulates an intracellular signal associated with costimulation (e.g., an activator of inositol phosphate 3-kinase) can be administered to a subject or, alternatively, T cells can be stimulated in vitro and then administered to a subject.

Another aspect of the invention pertains to screening assays for identifying inhibitors or activators of a phosphatidylinositol 3-kinase. In one embodiment, a T cell which expresses a cell surface receptor (e.g., CD28) which binds a costimulatory molecule is utilized. To identify an inhibitor, an intracellular signal transduction pathway associated with the receptor in the T cell is stimulated in the presence of an agent to be tested and an inhibitor is identified based upon its ability inhibit production of at least one D-3 phosphoinositide in a T cell. To identify an activator, the T cell is contacted with an agent to be tested and an activator is identified based upon its ability to stimulate production of at least one D-3 phosphoinositide in a T cell.

BRIEF DESCRIPTION OF THE DRAWINGS

FIG. 5 is a series of flow cytometric profiles from a cell-conjugate assay in which Jurkat cells were incubated either CHO-neo, CHO-B7-1 or CHO-B7-2 cells. Calcium flux is indicated on the Y-axis and cell conjugation is indicated on the X-axis.

FIG. 6 is a graphic representation of the effect of membrane-bound B7-1 and B7-2, in combination with an anti-CD3 antibody, on IL-2 production by purified human peripheral blood T cells, demonstrating a dose dependent increase in IL-2 production by costimulation with either B7-1 or B7-2.

FIG. 7B is a graphic representation of the percent inhibition by wortmannin (1 to 100 nM) of IL-production by human T cells stimulated for 24 hours with anti-CD3 antibody (OKT3) together with CHO cells expressing B7-1, B7-2 or both B7-1 and B7-2, or T cells stimulated with PMA together with CHO cells expressing B7-1 or B7-2.

DETAILED DESCRIPTION OF THE INVENTION

Figure 1:
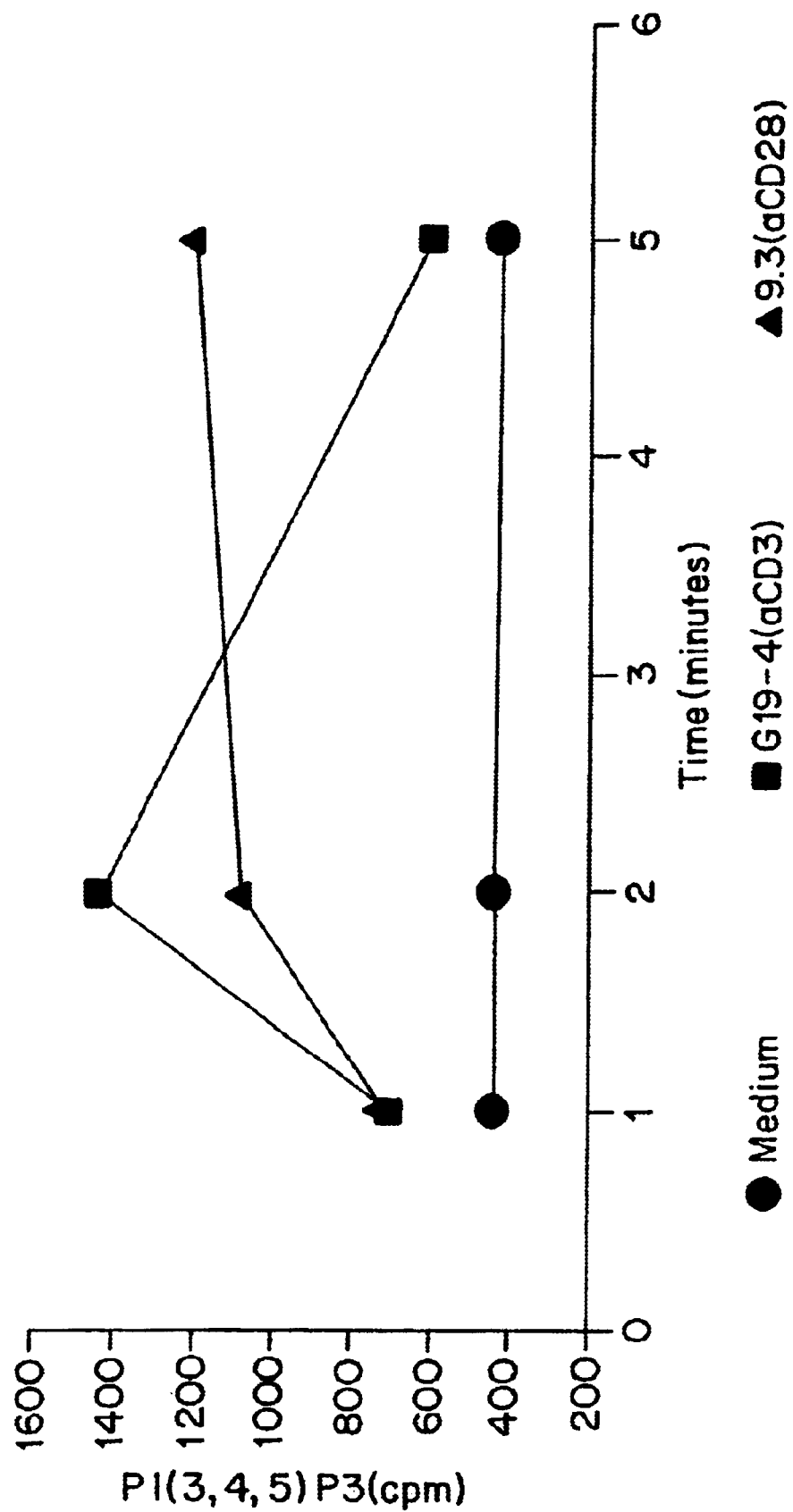
FIG. 1 is a graphic representation of the production of phosphatidylinositol(3,4,5)-triphosphate in $CD28^+$ T cells (Jurkat cells) following stimulation of the cells with medium, an anti-CD3 antibody or an anti-CD28 antibody, demonstrating distinct kinetics of phosphatidylinositol 3-kinase activation upon stimulation through CD3 or CD28.

This invention features methods for regulating T cell responses by modulating intracellular signals generated in a T cell upon costimulation, e.g. by binding of a surface receptor on the T cell to a costimulatory molecule. In particular, the invention pertains to modulation of the production of D-3 phosphoinositides in a T cell to inhibit or stimulate a costimulatory signal to thereby inhibit or stimulate T cell responses. Inhibition of a costimulatory signal by interfering with signal transduction associated with costimulation can further be used to induce T cell unresponsiveness. The invention is based, at least in part, on the discovery that stimulation of a T cell through the CD28 surface receptor leads to the production of D-3 phosphoinositides in a T cell and that an inhibitor of a phosphatidylinositol 3-kinase (also referred to herein as PI3K) inhibits production of D-3 phosphoinositides in the T cell upon CD28 ligation. The invention is further based, at least in part, on the discovery that inhibition of PI3K activity in a T cell inhibits T cell responses, such as cytokine production and cellular proliferation.

Accordingly, one aspect of the invention pertains to methods for inhibiting a response by a T cell by interfering with intracellular signal transduction associated with signal transduction. In one embodiment, an intracellular signal is inhibited by contacting a T cell expressing a cell surface receptor that binds a costimulatory molecule with an agent which inhibits production of D-3 phosphoinositides in the T cell. The term "a T cell expressing a cell surface receptor that binds a costimulatory molecule" is intended to encompass T cells expressing CD28 and/or CTLA4, or other receptor capable of binding a costimulatory molecule such as B7-1, B7-2 or other B7 family member.

A "response" by a T cell is intended to encompass T cell responses that occur upon triggering of a primary activation signal and a costimulatory signal in the T cell, and includes lymphokine production (e.g., IL-2 production) and T cell proliferation. Inhibition of a T cell response may involve complete blocking of the response (i.e., a lack of a response) or a reduction in the magnitude of the response (i.e., partial inhibition of the response).

The term "D-3 phosphoinositides" is intended to include derivatives of phosphatidylinositol that are phosphorylated at the D-3 position of the inositol ring and encompasses the compounds phosphatidylinositol(3)-monophosphate (PtdIns(3)P), phosphatidylinositol(3,4)-bisphosphate (PtdIns(3,4)$P_2$), and phosphatidylinositol(3,4,5)-trisphosphate (PtdIns(3,4,5)$P_3$).

D-3 phosphoinositides are generated intracellularly by the activity of a phosphatidylinositol 3-kinase (PI3K). Accordingly, in one embodiment, the agent which inhibits production of a D-3 phosphoinositide in the T cell is an agent which inhibits the activity of a PI3K. A preferred agent which inhibits PI3K activity in a T cell is the fungal metabolite wortmannin, or derivatives or analogues thereof. Wortmannin derivatives or analogues include compounds structurally related to wortmannin which retain the ability to inhibit PI3K and T cell responses. Examples of wortmannin derivatives and analogues are disclosed in Wiesinger, D. et al. (1974) *Experientia* 30:135–136; Closse, A. et al. (1981) *J. Med. Chem.* 24:1465–1471; and Baggiolini, M. et al. (1987) *Exp. Cell Res.* 169:408–418. Another inhibitor of PI3K activity that can be used is the bioflavenoid quercetin, or derivatives or analogues thereof. Quercetin derivatives or analogues include compounds structurally related to quercetin that retain the ability to inhibit PI3K and inhibit T cell responses. Examples of quercetin derivatives and analogues are disclosed in Vlahos, C. J. et al. (1994) *J. Biol. Chem.* 269:5241–5284. A preferred quercetin derivative which inhibits PI3K activity is LY294002 (described in Vlahos et al. cited supra). Alternatively, other inhibitors of PI3K, for example those identified by methods described below, can be used.

Another aspect of the invention involves inhibiting a response by a T cell by interfering with two or more intracellular signalling events associated with costimulation. For example, CD28 stimulation has been shown to result in protein tyrosine phosphorylation in the T cell (see e.g., Vandenberghe, P. et al. (1992) *J. Exp. Med* 175:951–960; Lu, Y. et al. (1992) *J. Immunol.* 149:24–29). Accordingly, in one embodiment, a T cell response is inhibited by contacting a T cell with a first agent which inhibits production of at least one D-3phosphoinositide in the T cell and with a second agent which inhibits tyrosine phosphorylation in the T cell. For example, the T cell can be contacted both with an agent which inhibits PI3K activity and with an agent which inhibits protein tyrosine kinase activity. A preferred protein tyrosine kinase inhibitor is one which inhibits src protein tyrosine kinases. In one embodiment, the src protein tyrosine kinase inhibitor is herbimycin A, or a derivative or analogue thereof. Derivatives and analogues of herbimycin A include compounds which are structurally related to herbimycin A and retain the ability to inhibit the activity of protein tyrosine kinases. In another embodiment, the agent which inhibits protein tyrosine phosphorylation is a protein tyrosine phosphatase or an activator of a protein tyrosine phosphatase. By increasing the tyrosine phosphatase activity in a T cell, the net amount of protein tyrosine phosphorylation is decreased. The protein tyrosine phosphatase can be a cellular protein tyrosine phosphatase within the T cell, such CD45 or Hcph. The activity of a cell surface tyrosine phosphatase on a T cell can be activated by contacting the T cell with a molecule which binds to the phsophatase and stimulates its activity. For example, an antibody directed against CD45 can be used to stimulate tyrosine phosphatase activity in a T cell expressing CD45 on its surface. Accordingly, in one embodiment, the agent which inhibits protein tyrosine phosphorylation within the T cell is an anti-CD45 antibody, or a fragment thereof which retains the ability to stimulate the activity of CD45. Examples of antibody fragments include Fab and F(ab')2 fragments. Antibodies, or fragments thereof, can be provided in a stimulatory form, for example multimerized or immobilized etc.

Other intracellular signals associated with costimulation can be inhibited together with inhibition of D-3 phosphoinositide production to inhibit T cell responses. For example, CD28 ligation has been associated with increased phospholipase C activity (see e.g., Nunes, J. et al. (1993) *Biochem. J.* 293:835–842) and increased intracellular calcium levels (see e.g. Ledbetter, J. A. et al. (1990) *Blood* 75:1531–1539 and the Examples). Accordingly, T cells can be contacted with both a first agent which inhibits PI3K activity and a second agent which inhibits phospholipase C activity and/or inhibits increases in intracellular calcium levels. As demonstrated in the Examples, the tyrosine kinase inhibitor herbimycin A also inhibits CD28-induced calcium flux in T cells.

T cell responses can be inhibited according to the methods of the invention either in vitro or in vivo. For example, an agent which inhibits D-3 phosphoinositide production in a T cell can be administered to a subject at a dose and for a period of time sufficient to inhibit T cell responses. Alternatively, T cells can be obtained from a subject, contacted with the agent in vitro and readministered to the subject. The term subject is intended to include animals in which immune responses occur, e.g., mammals, including humans, monkeys, dogs, cats, rabbits, rats, mice, and transgenic species thereof. Subjects in which T cell responses can be inhibited include subjects in which it is desirable to downmodulate an immune response. Downmodulation is intended to encompass both partial and complete inhibition of T cell responses, such as lymphokine production and T cell proliferation. The methods are applicable, for example, to a subject suffering from an autoimmune disease or other disorder associated with an abnormal immune response, or a transplant recipient, such as a recipient of a bone marrow transplant or other organ transplant.

In one embodiment of the invention, a costimulatory signal is inhibited in a T cell to induce antigen-specific T cell unresponsiveness. Accordingly, another aspect of the invention pertains to methods for inducing T cell unresponsiveness to an antigen. The term "T cell unresponsiveness" as used herein refers to a reduction in or lack of a T cell response (e.g., proliferation, lymphokine secretion or induction of effector functions) by a T cell upon exposure to an antigen (or antigenic portion) to which the T cell has been rendered unresponsive. The terms "T cell unresponsiveness" and "T cell anergy" are used interchangeably herein. T cell unresponsiveness to an antigen can be induced by triggering an antigen-specific primary activation signal in the T cell (e.g., activation through the TCR/CD3 complex) in the absence of a costimulatory signal. In the method of the invention, a costimulatory signal is blocked in a T cell by contacting the T cell with an agent which interferes with an intracellular signal associated with costimulation. Specifically, T cell unresponsiveness to an antigen can be induced by contacting an antigen-specific T cell (i.e., a T cell expressing a TCR which recognizes the antigen) with the antigen in a form suitable to trigger a primary activation signal in the T cell in the presence of an agent which inhibits production of D-3 phosphoinositides in the T cell to inhibit a costimulatory signal. The antigen can be, for example, an autoantigen which stimulates an autoimmune reaction or an alloantigen which stimulates rejection of transplanted cells. Preferably, the agent which inhibits production of D-3 phosphoinositides inhibits the activity of PI3K in the T cell, such as wortmannin or quercetin, or a derivative or analogue thereof (e.g., LY294002). Additional agents which inhibit other intracellular signals associated with costimulation (as discussed above) can also be used in conduction with an agent which inhibits production of D-3 phosphoinositides in the T cell. For example, the T cell can be contacted with a PI3K inhibitor together with a protein tyrosine kinase inhibitor, such as herbimycin A.

To induce T cell unresponsiveness, an antigen-specific T cell is contacted with an antigen in a form suitable to trigger a primary activation signal in the T cell, which means that the antigen is presented to the T cell such that a signal is triggered in the T cell through the TCR/CD3 complex. For example, the antigen can be presented to the T cell by an antigen presenting cell in conduction with an MHC molecule. A syngeneic antigen presenting cell, such as a B cell, macrophage, monocyte, dendritic cell, Langerhan cell, or other cell which can present antigen to a T cell, can be incubated with the T cell in the presence of the antigen such that the antigen presenting cell presents the antigen to the T cell. Alternatively, to induce anergy to alloantigens, the T cell can be incubated with an allogeneic cell, which presents alloantigens to the T cell.

To induce T cell unresponsiveness to an antigen in vivo, an agent which inhibits production of D-3 phosphoinositides in a T cell is administered to a subject at a dose and for a period of time sufficient to induce T cell unresponsiveness to the antigen. Following administration of the agent, antigen-specific T cells are contacted with the antigen endogenously (for example, an autoantigen expressed by cells endogenously). Alternatively, to induce T cell unresponsiveness to an antigen in vitro. In this case, T cells are obtained from a subject, contacted in vitro with the antigen together with the agent to induce antigenic unresponsiveness, and then readministered to the subject. For example, T cells obtained from a transplant recipient can be contacted with allogeneic cells from a graft donor together with an agent which inhibits D-3 phosphoinositide production in the T cells (e.g., wortmannin, quercetin, LY294002) prior to transplantation of the graft into the recipient to induce alloantigen-specific T cell unresponsiveness. The recipient T cells which have been rendered unresponsive to the donor antigens are then readministered to the recipient. Alternatively, in the case of bone marrow transplantation, bone marrow to be transplanted (including any residual T cells) can be contacted in vitro with allogeneic cells from the bone marrow recipient together with an agent which inhibits D-3 phosphoinositide production to induce unresponsiveness in the donor T cells to recipient alloantigens. This pretreatment can be performed to inhibit graft versus host disease.

The methods for inducing T cell unresponsiveness can be applied therapeutically in situations where it is desirable to downmodulate an immune response, such as transplantation, including organ transplants and bone marrow transplants (as discussed above), and autoimmune diseases and other disorders associated with an abnormal immune response. Examples of autoimmune diseases or disorders associated with an inappropriate or abnormal immune response include rheumatoid arthritis, juvenile rheumatoid arthritis, psoriatic arthritis, allergies, contact dermatitis, psoriasis, leprosy reversal reactions, erythema nodosum leprosum, autoimmune uveitis, multiple sclerosis, allergic encephalomyelitis, systemic lupus erythematosus, acute necrotizing hemorrhagic encephalopathy, idiopathic bilateral progressive sensorineural hearing loss, aplastic anemia, pure red cell anemia, idiopathic thrombocytopenia, polychondritis, scleroderma, Wegener's granulomatosis, chronic active hepatitis, myasthenia gravis, Stevens-Johnson syndrome, idiopathic sprue, lichen planus, Crohn's disease, Graves ophthalmopathy, sarcoidosis, primary biliary cirrhosis, primary juvenile diabetes, dry eye associated with Sjögren's syndrome, uveitis posterior, and interstitial lung fibrosis.

Another aspect of the invention pertains to stimulating a T cell response by providing a costimulatory signal to a T cell. Delivery of a costimulatory signal, in conjuction with a primary activation signal, can generate a T cell response. In the method of the invention, a costimulatory signal is provided by contacting a T cell which has received a primary activation signal with an agent which stimulates production of D-3 phosphoinositides in the T cell. A T cell "response" is intended to encompass production of at least one lymphokine by the T cell (e.g., IL-2 ) and/or proliferation by the T cell. A primary activation signal can delivered to a T cell by stimulating the T cell through the TCR/CD3 complex, for example by anti-CD3 antibodies or by an MHC/antigen complex, or by use of an agent which mimics this stimulation, for example a phorbol ester (e.g., PMA). The term "agent", as used herein, is intended to encompass chemicals and other pharmaceutical compounds which stimulate a costimulatory signal in a T cell without the requirement for an interaction between a T cell surface receptor and a costimulatory molecule. For example, the agent may act intracellularly to stimulate a signal associated with costimulation. In one embodiment, the agent is a non-proteinaceous compound. As the agent used in the method is intended to bypass the natural receptor:ligand costimulatory mechanism, the term agent is not intended to include a cell expressing a natural ligand of CD28/CTLA4 (e.g., expressing B7-1 and/or B7-2).

Preferably, production of D-3 phosphoinositides in the T cell is stimulated by contacting the T cell with an activator of PI3K. Activators of PI3K can be identified, for example, by methods described below. Additional agents which stimulate one or more other intracellular signals associated with costimulation can be used in conjuction with an inhibitor of D-3 phosphoinositide production. For example, the T cell can be contacted both with a first agent which stimulates PI3K activity and a second agent which stimulates protein tyrosine phosphorylation within the T cell. Protein tyrosine phosphorylation can be stimulated in the T cell, for example, by contacting a T cell with an activator of protein tyrosine kinases, such as pervanadate (see O'Shea, J. J. et al. (1992) *Proc. Natl. Acad. Sci. USA* 89:10306–103101; and Secrist, J. P. (1993) *J. Biol. Chem.* 268:5886–5893). Alternatively, the T cell can be contacted both with an activator of PI3K and with an agent which inhibits the activity of a cellular protein tyrosine phosphatase, such as CD45, to increase the net amount of protein tyrosine phosphorylation in the T cell. The method also encompasses stimulation of other intracellular signals associated with costimulation of a T cell, such as stimulation of phospholipase C activity and/or increases in intracellular calcium levels.

Another embodiment of the invention provides a method for stimulating a specific response to an antigen by an antigen-specific T cell. To stimulate a T cell response, an antigen-specific T cell is contacted with the antigen together with an agent which stimulates production of D-3 phosphoinositides in the T cell, thereby triggering a costimulatory signal in the T cell. Preferably, the agent which stimulates production of D-3 phosphoinositides in the T cell is an activator of PI3K. The T cell is contacted with the antigen in a form suitable for stimulating a primary activation signal in the T cell (e.g., through the TCR/CD3 complex), such as in conjuction with an MHC molecule. An antigen presenting cell (e.g., a B cell, macrophage, monocyte, dendritic cell, Langerhan cell, or other cell which can present antigen to a T cell) can be incubated with the T cell in the presence of the antigen (e.g., a soluble antigen). Alternatively, a cell expressing an antigen of interest can be incubated with the T cell. For example, a tumor cell expressing tumor-associated antigens can be incubated with a T cell together with an agent which induces an intracellular costimulatory signal to induce a tumor-specific response. Alternatively, a cell infected with a pathogen, e.g. a virus, which presents antigens of the pathogen can be incubated with a T cell in the presence of the agent. In addition to stimulating production of D-3 phosphoinositides in the T cell, the T cell can be contacted with one or more other agents which stimulate one or more additional intracellular signals associated with CD28 ligation, for example an activator of a protein tyrosine kinase, such as pervanadate.

An agent which stimulates a CD28-associated intracellular signal in T cells, e.g., an activator of PI3K, can be administered to a subject in vivo, or alternatively, a T cell can be obtained from a subject, stimulated in vitro, and readministered to the subject. The methods for stimulating T cell responses are useful in therapeutic situations where it is desirable to upregulate an immune response (e.g., induce a response or enhance an existing response). For example, the method can be used to enhance a T cell response against tumor-associated antigens. Tumor cells from a subject typically express tumor-associated antigens but may be unable to stimulate a costimulatory signal in T cells (e.g., because they lacks expression of costimulatory molecules). Thus, tumor cells can be contacted with T cells from the subject together with an agent which stimulates D-3 phosphoinositides in the T cell to trigger a costimulatory signal in the T cell. Alternatively, T cells can be stimulated as described herein to induce or enhance responsiveness to pathogenic agents, such as viruses (e.g., human immunodeficiency virus), bacteria, parasites and fungi. Additionally, the efficacy of vaccines against such pathogenic agents can be enhanced. For example, an agent which stimulates D-3phosphoinositide production in T cells can be administered to a subject infected with a pathogenic agent or can be coadministered with a vaccine to enhance the responsiveness of T cells to antigens of the vaccine. Alternatively, T cells can be cultured in vitro which antigen presenting cells which express an antigen(s) from a pathogenic agent together with an agent which stimulates an intracellular signal associated with costimulation (e.g., an activator of PI3K).

Another application of the method for stimulating T cell responses pertains to patients who have impaired signal transduction through CD28 and/or other cell surface molecule(s) associated with costimulation (e.g., CTLA4). For example, a patient with idiopathic thrombocytopenia has been reported to exhibit defective CD28-mediated signal transduction, presumably due to a congenital defect (see Perez-Blas, M. et al. (1991) *Clin. Exp. Immunol.* 85:424–428). In patients having defective CD28 signalling ability, it may be possible to bypass the defect and restore CD28-dependent T cell activation by contacting T cells from the patient with one or more agents which stimulate intracellular signals generated upon normal CD28 ligation. For example, a patient having a defect resulting in reduced or a lack of D-3 phosphoinositide production upon CD28 ligation can be treated by contacting T cells from the patient with an agent which stimulates production of D-3 phosphoinositides in the T cells.

Another aspect of the invention pertains to screening assays for identifying inhibitors and activators of PI3K which can then be used to inhibit or stimulate, respectively, T cell responses. PI3K is a heterodimer consisting of a regulatory and a catalytic subunit. Two forms of the enzyme which preferentially use PtdIns(4,5)$P_2$ as a substrate and are inhibitable by wortmannin have been described (see Otsu, M et al. (1991) *Cell* 65:91–104; Hu, P. et al. (1993) *Mol. Cell. Biol.* 13:7677–7688; and Hiles, I. D. et al. (1992) *Cell* 70:419). Another form of the enzyme which preferentially uses PtdIns as a substrate and is not inhibitable by wortmannin has also been described (see Stephens, L. et al. (1994) *Curr. Biol.* 4:203–214). It will be appreciated that identification of specific inhibitors or activators of PI3K must be specific to the appropriate intracellular form(s) of PI3K involved in costimulatory signals to avoid unwanted or adverse side effects. Thus, agents which specifically inhibit or activate a form(s) of PI3K involved in costimulation (e.g., a form which is also inhibitable by wortmannin) are preferable.

In one embodiment, a screening assay of the invention is based upon the ability of an inhibitor or activator of a PI3K to inhibit or stimulate, respectively, the production of at least one D-3 phosphoinositides in a T cell (preferably PtdIns(3,4,5)$P_3$). To identify an inhibitor of a PI3K, a T cell is stimulated through a cell surface receptor that binds a costimulatory molecule (i.e., a T cell which has received a costimulatory signal) in the presence and absence of a substance to be tested. Preferably, a T cell which expresses CD28 is used in the assay. Alternatively, a T cell which expresses CTLA4 can be used. A costimulatory signal can be stimulated in the T cell by contacting the T cell with a ligand for CD28 or CTLA4. Preferably, the ligand is a physiologic ligand, such as membrane-bound B7-1 or B7-2, rather than antibodies directed against the T cell surface receptor. A cell which naturally expresses B7-1 and/or B7-2 can be used or more preferably a cell (e.g., a CHO cell) which is transfected to express a costimulatory molecule is used. In the presence of an inhibitor of PI3K, stimulation of a T cell through a surface receptor which binds a costimulatory molecule (e.g., CD28) results in reduced production of D-3 phosphinositides in the T cell relative to stimulation in the absence of the inhibitor. Production of D-3 phosphoinositides in the T cell can be measured by any suitable method known in the art. For example, production of D-3 phosphoinositides in the T cell can be measured by high pressure liquid chromatography (as described in the Examples). Alternatively, D-3 phosphoinositide production can be assessed by thin layer chromatography, e.g. as described in Okada, T. et al. (1994) *J. Biol. Chem.* 269:3563–3567. D-3 phosphoinositides whose intracellular production can be assessed include PtdIns(3)P, PtdIns(3,4)$P_2$ and PtdIns(3,4,5)$P_3$. Preferably, production of PtdIns(3,4,5)$P_3$ in the T cell is detected in the presence or absence of the substance to be tested.

To identify an activator of a PI3K, a T cell which expresses a cell surface receptor which binds a costimulatory molecule is contacted with a substance to be tested. An activator of a PI3K is identified based upon its ability to stimulate production of at least one D-3 phosphoinositides in a T cell (preferably PtdIns(3,4,5)$P_3$). Thus, in the presence of a PI3K activator, the amount of a D-3 phosphoinositide in the T cell is increased relative to the amount of the D-3 phosphoinositide in the T cell in the absence of the substance. Production of D-3 phosphoinositides (e.g., PtdIns(3)P, PtdIns(3,4)$P_2$ and/or PtdIns(3,4,5)$P_3$) in the T cell can be assessed by standard methods, such as high pressure liquid chromatography or thin layer chromatography, as discussed above.

In another embodiment of the screening assays of the invention, the ability of a substance to directly inhibit or stimulate the activity of a PI3K isolated from a cell is assessed and then a substance identified as an inhibitor or activator of the PI3K is contacted with a T cell to determine the ability of the substance to inhibit or stimulate a T cell response. For example, an isolated PI3K is incubated with a substrate (e.g. PtdIns(4,5)$P_2$) in the presence of a radiolabeled phosphate donor and a substance to be tested. An inhibitor of the kinase activity of the PI3K will cause reduced phosphorylation of the substrate (relative to phosphorylation in the absence of the inhibitor), whereas an activator will cause increased phosphorylation of the substrate (relative to phosphorylation in the absence of the activator). An inhibitor or activator so identified in vitro is then contacted with a T cell to determine the ability of the inhibitor or activator to inhibit or stimulate, respectively, a T cell response (e.g., IL-2 production).

Other Embodiments

Other cells types in addition to T cells have been described which express CD28 on their surface. These cell types include plasma cells (see Kozbor, D. et al. (1987) *J. Immunol.* 138:4128–4132) and bone marrow-derived mast cells. Stimulation of other CD28[+] cells types through CD28 may al so lead to production of D-3 phosphoinositides in the cells and generation of specific cell responses. Inhibition or activation of D-3 phosphoinositide production in these cells, by the methods described herein, may also be useful for inhibiting or stimulating responses by other CD28[+] cell types.

This invention is further illustrated by the following examples which should not be construed as limiting. The contents of all references, patents and published patent applications cited throughout this application are hereby incorporated by reference.

EXAMPLE 1

Ligation of CD28 Stimulates Production of D-3 Phosphoinositides

In this example, the production of D-3 phosphoinositides in CD28[+] Jurkat cells upon stimulation of the Jurkat cells through CD28 or CD3 was examined. Jurkat cells were labeled with carrier-free [$^{32}$P]-orthophosphate ([$^{32}$Pi]) as follows: Jurkat cells were washed 3 times in phosphate-free media (DMEM/RPMI) and incubated for 10 minutes at 37° C. for 10 minutes between washes. The cells were resuspended in 10 ml phosphate-free media containing 20 mM HEPES, pH 7.4 and 5% dialysed fetal calf serum (dialysed overnight against saline). Carrier-free [$^{32}$Pi] was added to the cells (1 mCi/10 ml cells) and the cells were incubated at 37° C. for 4 to 6 hours. After labeling, cells were washed 3 times with phosphate-free media and resuspended in RPMI 1640 containing 20 mM HEPES.

In various experiments, aliquots of [$^{32}$Pi]-labeled Jurkat cells (0.15 ml; 2×10$^7$ cells) were stimulated with media alone, an anti-CD3 antibody (G19-4), an anti-CD28 antibody (9.3), untransfected CHO cells, or CHO cells transfected to express a CD28 ligand, either human B7-1 (CHO-B7-1) or B7-2 (CHO-B7-2). [obtained from Drs. G. Freeman and L. Nadler; CHO cells were transfected with a recombinant expression vector containing a cDNA encoding human B7-1, the sequence of which is disclosed in Freeman, G. J. et al. (1989) *J. Immunol.* 143:2714–2722, or a cDNA encoding human B7-2, the sequence of which is disclosed in Freeman, G. J. et al. (1993) *Science* 262:909–911, by standard techniques). For stimulation with CHO cells, Jurkat cells were incubated with 10$^7$ CHO cells and cell contact was achieved by low speed centrifugation in a microfuge for 5 seconds. At various time intervals following stimulation (ranging between about 1 and 25 minutes), the cells were lysed and phospholipids were extracted, deacylated and separated by anion exchange HPLC basically as described in Ward, S. G et al. (1992) *J. Immunol.* 22:45, with modifications as described below.

The incubations were terminated by addition of 750 µl CHCl$_3$/methanol/water (32.6%/65.3%/2.1% v/v/v). Once cell reactions were quenched, the samples were kept on ice during subsequent extractions. Phases were separated by addition of 725 µl CHCl$_3$ (containing 10 mg Folch lipids; e.g., from Sigma, Catalogue No. B1502) and 172 µl 2.4 M HCl, 5 mM tetrabutylammonium sulphate to each sample. The samples were vortexed and centrifuged for 5 minutes at 1000 rpm to separate phases. The lower phase was removed and added to a tube containing ½ volume of 1 M HCl, 25 mM Na$_2$EDTA, pH 7.0, 5 mM tetrabutylammonium sulphate. The samples were recentrifuged to separate phases, the bottom layer was removed and placed in a clean tube, and the sample was dried down in vacuo. Samples were deacylated by adding 1 ml methylamine reagent (40% in water/methanol/n-butanol 4:4:1 v/v/v), vortexing and incubating at 53° C. for 40 minutes. Samples were placed on ice and then dried down in vacuo. The samples were resuspended in 0.5 ml sterile distilled water and vortexed to mix. The samples were extracted twice with 0.7 ml n-butanol:40–60% petroleum ether/ethyl formate (20:4:1 v/v/v). The bottom aqueous phase was dried in vacuo and stored at −70° C. prior to HPLC analysis.

HPLC was performed using a gradient based on buffers A (water)/B [1.25 M (NH$_4$)$_2$HPO$_4$] (adjusted to pH 3.8 with $H_3PO_4$ at 25° C.) and a Partisphere SAX column (commercially obtained from Whatman). Deacylated phospholipid samples were resuspended in 0.1 ml distilled water and injected onto the column. The eluate was fed into a Canberra Packard A-500 Flo-One on-line beta-radiodetector, where it was mixed with three parts Flo-Scint IV scintillation cocktail and the results were analyzed on the Flo-One data program (Radiomatic, USA). Eluted peaks were compared to retention times for standards prepared from [$^3$H]PtdIns, [$^3$H]PtdIns(4)P and [$^3$H]PtdIns(4,5)P$_2$ (commercially obtained from Amersham International). Standard [$^{32}$P]PtdIns(3)P, [$^{32}$P]PtdIns(3,4)P$_2$ and [$^{32}$P]PtdIns(3,4,5)P$_3$ were prepared by incubating isolated phosphatidylinositol 3-kinase with PtdIns (commercially obtained from Sigma) as described in Ward, S. G. et al. (1992) *J. Biol. Chem.* 267:23862.

The production of PtdIns(3,4,5)P$_3$ in Jurkat cells following stimulation with anti-CD3 or anti-CD28 antibodies for 1–5 minutes is shown in FIG. 1. The results demonstrate that while stimulation through either CD3 or CD28 induces PtdIns(3,4,5)P$_3$ production, the induction kinetics for the two pathways are distinct. Upon CD3 stimulation, PI3K activation (as assessed by PtdIns(3,4,5)P$_3$ production) increases early (i.e., within 2 minutes) and is transient (i.e., returns to baseline by 5 minutes). In contrast, PI3K activation induced by CD28 stimulation is delayed compared to CD3 stimulation (i.e., is not maximal until 5 minutes or later) and persists longer than that induced by CD3 stimulation. These results indicate that distinct mechanisms are involved in PI3K activation mediated by either CD3 or CD28 ligation.

Figure 2:
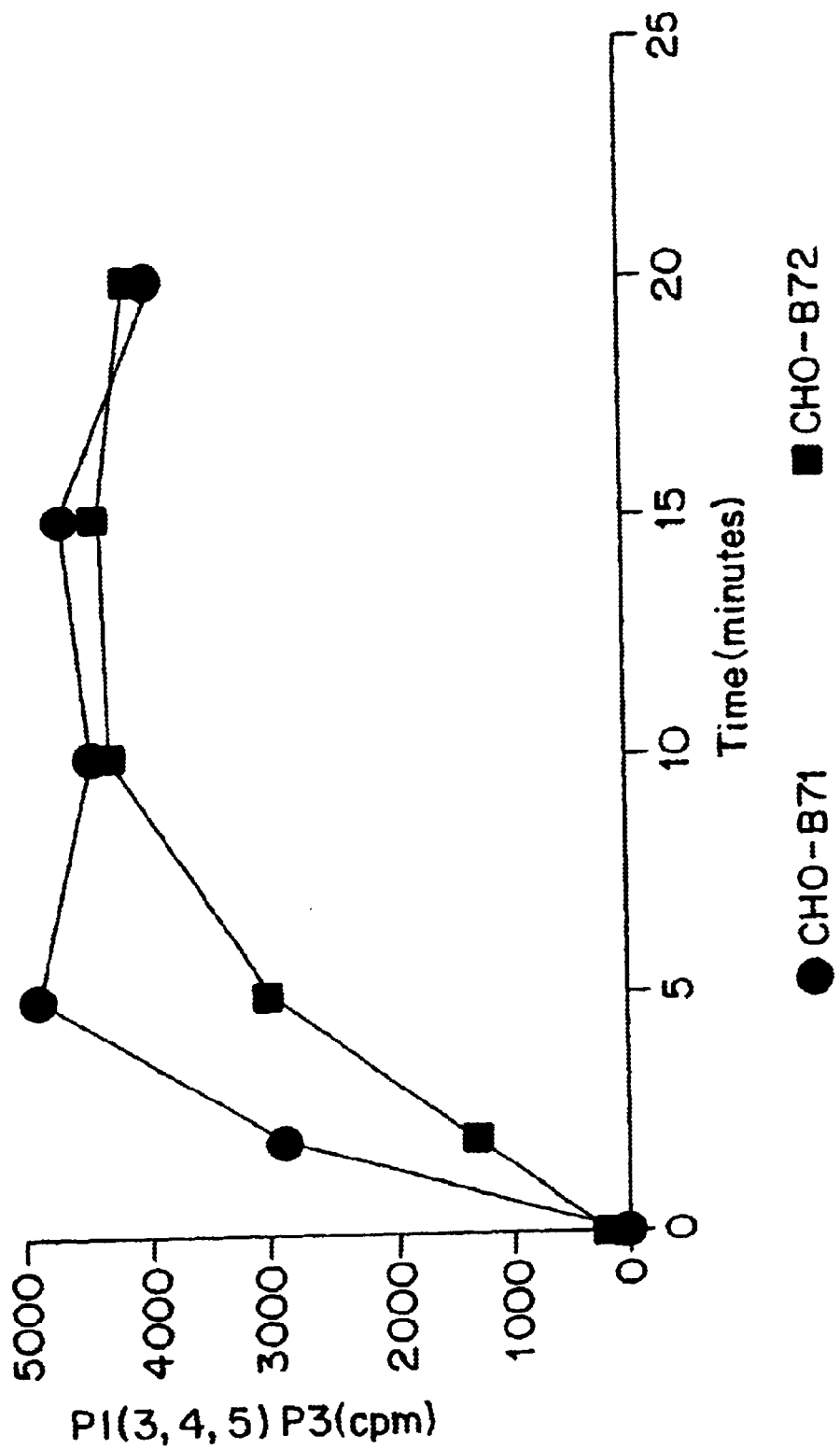
FIG. 2 is a grahic representation of the production of phosphatidylinositol(3,4)-bisphosphate in $CD28^+$ T cells (Jurkat cells) following stimulation of the cells with CHO cells transfected to express B7-1 or B7-2, demonstrating distinct kinetics of phosphatidylinositol 3-kinase activation upon stimulation with B7-1 or B7-2.

The production of PtdIns(3,4,5)P$_3$ in Jurkat cells following stimulation with CHO-B7-1 or CHO-B7-2 cells for 0–20 minutes is shown in FIG. 2. The results indicate that stimulation of CD28 with either B7-1 and B7-2 induces potent activation of PI3K (as assessed by PtdIns(3,4,5)P$_3$ production). The induction kinetics are slightly different for the two CD28 ligands: B7-1 stimulates activation earlier than B7-2, although both plateau to the same level. Stimulation of PtdIns(3,4,5)P$_3$ production by either B7-1 and B7-2 is very strong and persistent (ie., continues for more than 20 minutes).

This example demonstrates that stimulation of T cells through CD28, either by its natural ligands B7-1 and B7-2 or by an anti-CD28 antibody, induces the production of D-3 phosphoinositides within T cells, indicating activation of PI3K upon CD28 ligation. In addition, this example demonstrates that CD28 shares in common B7-1 and B7-2 as physiological ligands, since Jurkat cells are CD28$^+$ but CTLA4$^-$ and cannot be induced to express CTLA4 (as shown in Lindsten, T. (1993) J. Immunol. 151:3489–3499). Thus, CTLA4 apparently is not required for B7-induced signal transduction and both B7-1 and B7-2 are physiologic ligands for CD28.

EXAMPLE 2

Figure 3:
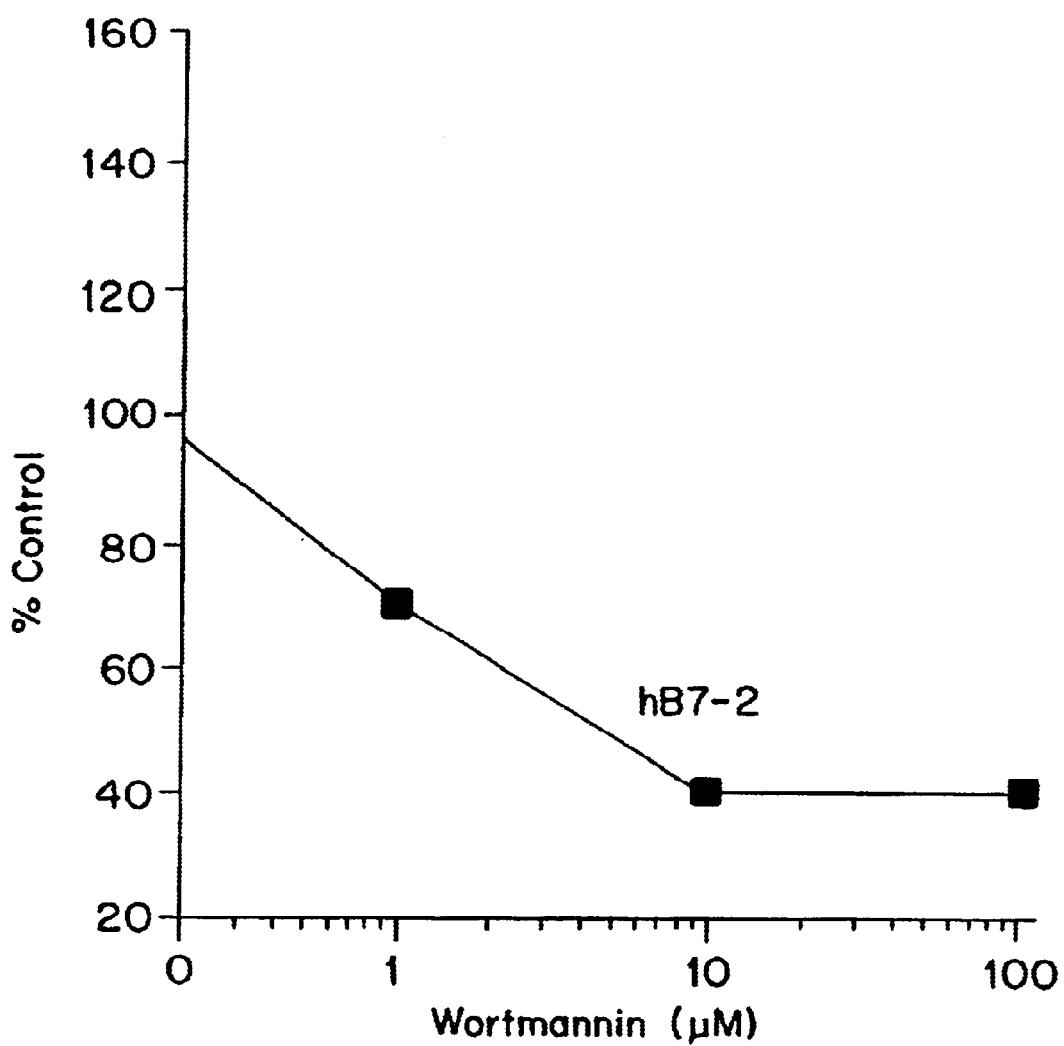
FIG. 3 is a graphic representation of the effect of various concentrations of wortmannin (0–100 $\mu$M) on production of phosphatidylinositol(3,4,5)-triphosphate in $CD28^+$ T cells (Jurkat cells_following stimulation of the cells with CHO cells transfected to express B7-2.

A Phosphatidylinositol 3-Kinase Inhibitor Can Inhibit Production of D-3 Phosphoinositides Induced by CD28 Ligation In this example, the effect of an inhibitor of phosphatidylinositol 3-kinase on CD28-mediated production of D-3 phosphoinositides within Jurkat cells was examined. Jurkat cells were labeled with orthophosphate and stimulated with CHO cells transfected to express B7-2, as described in Example 1. Additionally, during stimulation, the cells were incubated in the presence of various concentrations (0–100 µM) of the fungal metabolite wortmannin, which is an inhibitor of phosphatidylinositol 3-kinase. Wortmannin was obtained commercially from Sigma Chemical Co. and stored as a 10 mM solution in DMSO at −40° C. It was diluted in medium immediately before addition to cells in culture. Following stimulation in the presence or absence of wortmannin, the amount of PtdIns(3,4,5)P$_3$ produced in the cells was measured by HPLC, as described in Example 1. The results are shown in FIG. 3, wherein the amount of PtdIns(3,4,5)P$_3$ detected in wortmannin-treated Jurkat cells upon stimulation with CHO-B7-2 is plotted graphically as a percentage of the amount of PtdIns(3,4,5)P$_3$ detected in untreated Jurkat cells stimulated with CHO-B7-2. The results demonstrate that treatment of Jurkat cells with increasing concentrations of wortmannin decreases the amount of D-3 phosphoinositides produced in the cells upon ligation of CD28 with B7-2. Accordingly, this example demonstrates that the generation of D-3 phosphoinositides intracellularly as a result of stimulation of T cells through CD28 can be inhibited by inhibiting the activity of phosphatidylinositol 3-kinase within the T cells.

EXAMPLE 3

Effect of Pharmacological Inhibitors on CD28-Mediated Calcium Flux

Figure 4:
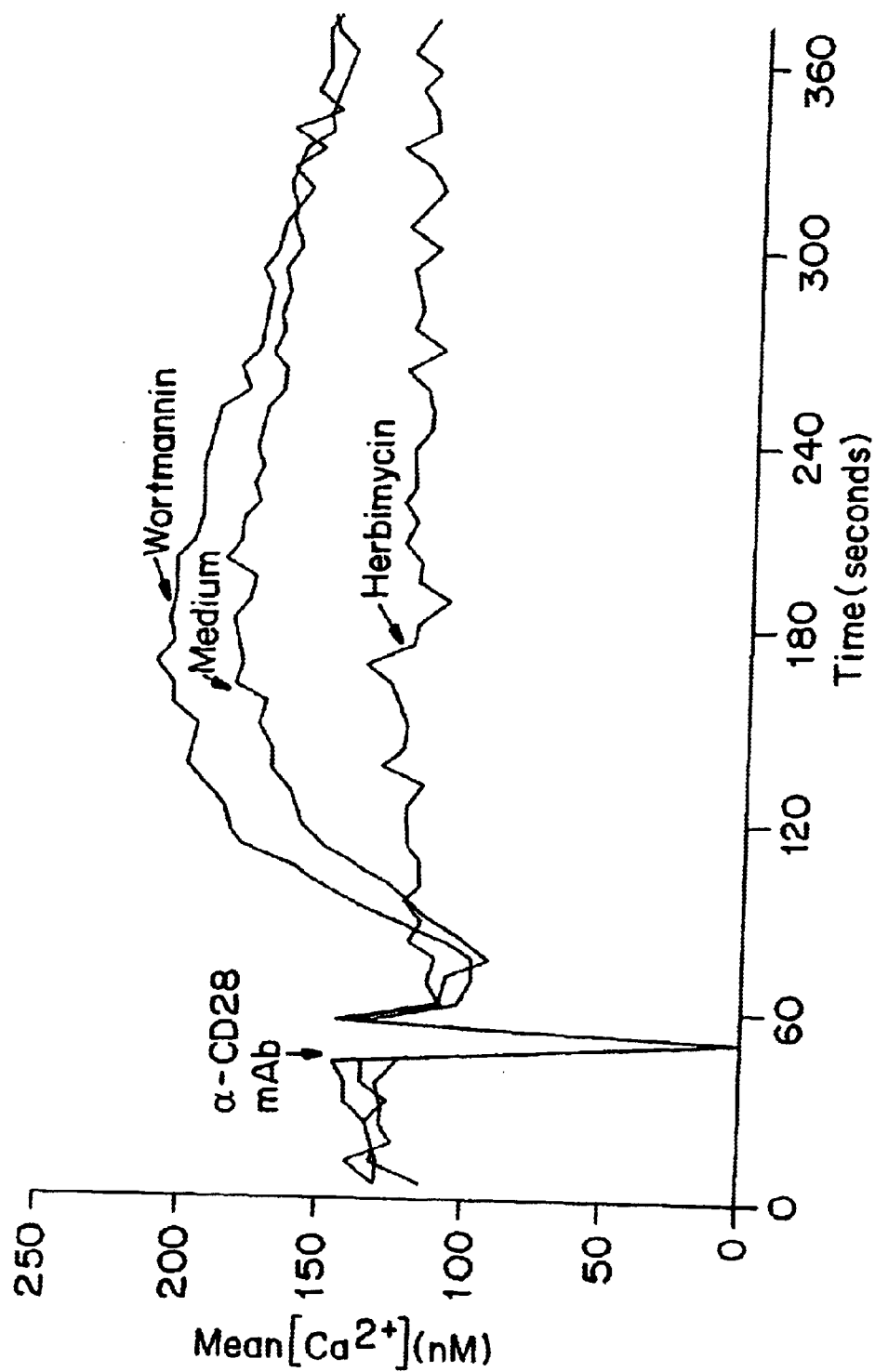
FIG. 4 is a graphic representation of the effect of wortmannin or herbimycin on calcium influx in T cells induced by ligation of CD28 with an anti-CD28 antibody.

In this example, the effect of pharmacological inhibitors on calcium flux in Jurkat cells induced by anti-CD28 antibodies was examined. The pharmacological inhibitors studied were wortmannin, which inhibits the activity of PI3K, and herbimycin A, which inhibits the activity of protein tyrosine kinases. Jurkat cells were stimulated with an anti-CD28 antibody, either in medium alone or in the presence of wortmannin or herbimycin A, and the mean calcium concentration (nM) in the cells was measured over several minutes following stimulation. As illustrated in FIG. 4, herbimycin A was capable of inhibiting CD28 antibody-induced calcium flux. In contrast, wortmannin was unable to inhibit CD28-antibody induced calcium flux. These results indicate that the effects of wortmannin on T cells are not mediated by interfering with calcium flux. Furthermore, given results described below in Example 5 showing that wortmannin inhibits costimulation as measured by IL-2 production induced by B7-1 or B7-2, this data indicates that measurement of CD28-induced calcium elevation is likely to be a misleading read-out for assessing compounds that specifically induce T cell unresponsiveness (i.e., anergy) or costimulation.

EXAMPLE 4

Induction of Calcium Flux by Natural CD28 Ligands

In this example, adhesion of CHO-B7-1 or CHO-B7-2 to Jurkat cells and induction of calcium mobilization in Jurkat cells in response to stimulation with CHO-B7-1 and B7-2 were examined. A flow cytometic cell calcium-conjugate assay, as described in Abe, R. et al. (1992) *J. Exp. Med.* 176:459–468, was used. In the cell conjugate assay, T cells are loaded with the calcium sensitive fluorescent probe indo-1 (which generates blue and green signals). CHO cells transfected with a control plasmid (CHO-neo) or CHO cells transfected to express B7-1 or B7-2 are loaded with the tracer dye DilC22(3) (which generates red signals; obtained commercially from Molecular Probes). Jurkat cell-CHO cell conjugates are analyzed by flow cytometry. Conjugates consisting of T cells and CHO cells can be measured by gating on red signals and calcium levels can be measured in the T cells by gating on the blue and green signals. The results are displayed as a series of two paramater dot plots, shown in FIG. 5. Calcium (indo-1 ratio) is on the Y axis and cell conjugates (red tracer) is on the X axis. Cells in the upper right quadrant represent Jurkat cells having high levels of calcium conjugated to CHO cells. Cells in the lower right quadrant represent Jurkat cells having normal calcium levels conjugated to CHO cells. Cells in the upper and lower left quadrants represent non-conjugated Jurkat cells having high or low levels of calcium, respectively.

The data indicates that both B7-1 and B7-2 can mediate adhesion to Jurkat cells. However, both ligands are poor at causing increases in calcium mobilization. Therefore, B7-1 and B7-2 are much more efficient at inducing PI3K activation (see Example 1) than calcium mobilization. In contrast, anti-CD28 antibodies are capable of stimulating both PI3K activation (see Example 1) and calcium flux (see Example 3). Thus, it appears that there are differences in the intracellular signals generated through CD28 ligation, depending upon whether natural ligands (e.g., B7-1 or B7-2) or antibodies are used for stimulation. It has previously been described (Nunes, J. et al. (1993) Int. Immunol. 5:311–315) that CD28 antibodies can have multiple and distinct effects on biochemical aspects of T cell signal transduction and activation (e.g., IL-2 production). These observations further indicate that it was not possible to predict the biochemical effects of natural ligands of CD28 (i.e., membrane-bound B7-1 and B7-2) on production of D-3 metabolites, as described herein, based upon extrapolation from previous results with CD28 antibodies.

EXAMPLE 5

A Phosphatidylinositol 3-Kinase Inhibitor Can Inhibit Production of Interleukin-2 Induced by CD28 Ligation In this example, the effect of an inhibitor of phosphatidylinositol 3-kinase on CD28-dependent production of interleukin-2 by T cells was examined. In a first series of experiments, the effect of T cell stimulation through CD28, in conjunction with stimulation through CD3, on IL-2 production was assessed in the absence of wortmannin. Highly purified human peripheral blood T cells were incubated for 24 hours with an immobilized anti-CD3 antibody (OKT3) alone or together with either an anti-CD28 antibody (9.3) or mitomycin C-treated CHO cells, either untransfected or transfected to express B7-1 or B7-2. Increasing numbers of CHO cells were tested ($0.5 \times 10^6$ to $4 \times 10^6$). After culture for 24 hours, the culture supernatants were assayed for IL-2 production by ELISA by standard techniques. As shown in FIG. 6, cells incubated in medium alone, OKT3 alone, or OKT3 together with untransfected CHO cells did not produce IL-2. In contrast, culture of the cells with OKT3 together with CHO cells expressing B7-1 or B7-2 stimulated IL-2 production in a dose dependent manner. Culture with OKT3 and 9.3 antibodies also stimulated IL-2 production. These results confirm that CD28 ligation, such as by B7-1 or B7-2 stimulation, can provide a costimulatory signal for lymphokine production.

Figure 7A:
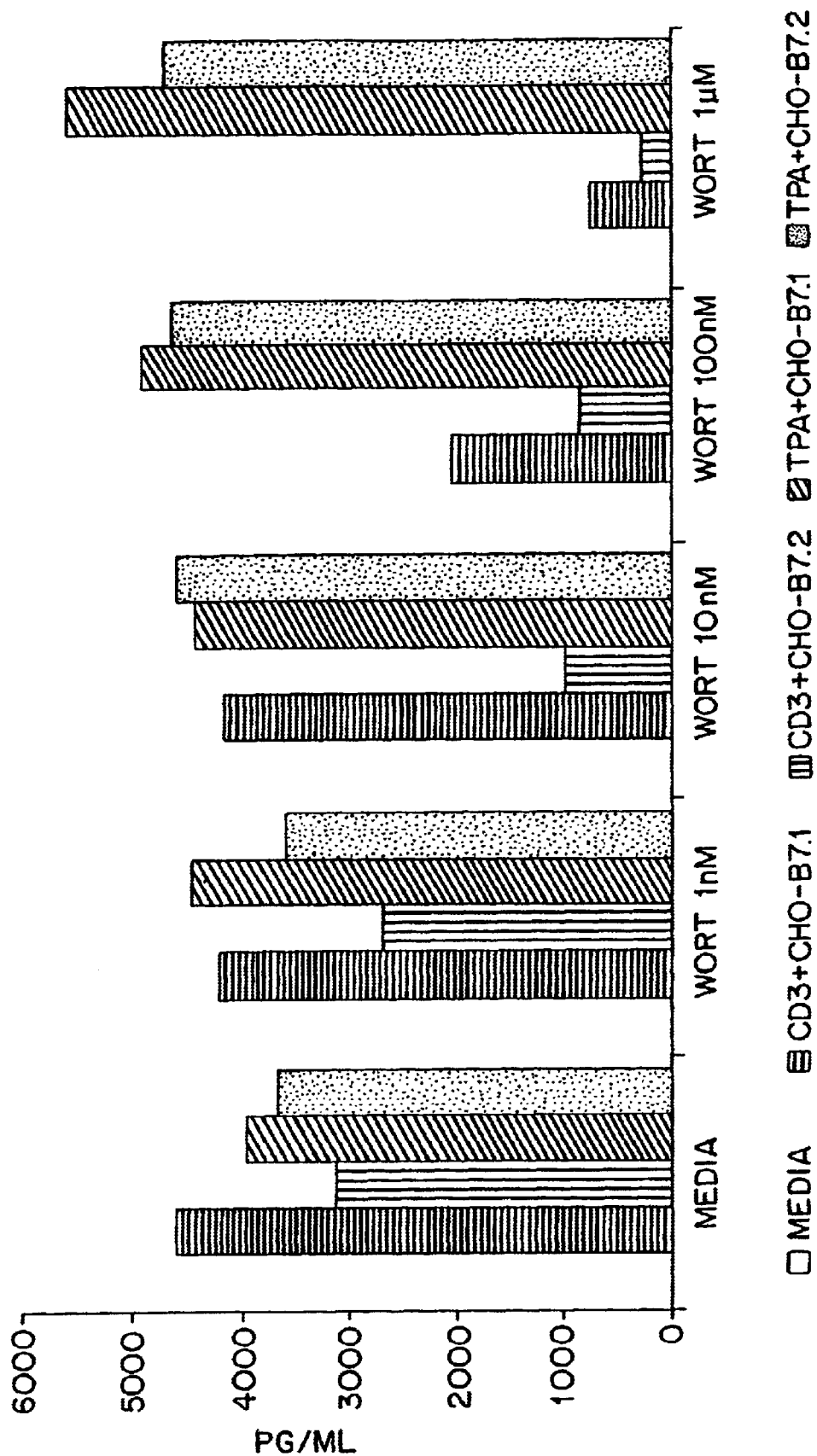
FIG. 7A is a graphic representation of the effect of wortmannin treatment (1 nM to 1 $\mu$M) on IL-2 production by resting human T cells 24 hours after stimulation of the cells with media, immobilized anti-CD3+CHO-B7-1, immobilized anti-CD3+CHO-B7-2, PMA+CHO-B7-1 or PMA+CHO-B7-2.

In a next series of experiments, resting human T cells were stimulated with either: 1) immobilized OKT3+CHO-B7-1, 2) immobilized OKT3+CHO-B7-2, 3) immobilized OKT3+CHO-B7-1+B7-2, 4) PMA+CHO-B7-1 or 5) PMA+B7-2. Stimulation of T cells was performed in media alone or in media containing wortmannin at concentrations between 1 nM and 1 μM. Twenty-four hours following culture, the supernatants were assayed for IL-2 production by ELISA. The results are shown in FIGS. 7A and 7B. The results indicate that wortmannin can inhibit IL-2 production stimulated by either B7-1 or B7-2 in conjunction with CD3 stimulation. Wortmannin-mediated inhibition of IL-2 production was dose dependent. The $ID_{50}$ for inhibition of B7-2-mediated stimulation was approximately 10 nM. The $ID_{50}$ for inhibition of B7-1-mediated stimulation was between 10 and 100 nM. These doses of wortmannin are not generally toxic to the cells and do not inhibit IL-2 production by a non-specific mechanism, as evidenced by the fact that IL-2 production stimulated by PMA together with membrane-bound B7-1 or B7-2 was not inhibited by wortmannin at concentrations as high as 1 μM. This example demonstrates that T cell activation, as assessed by production of IL-2 in response to stimulation through the TCR/CD3 complex and CD28, can be inhibited by treatment of the T cell with an agent which inhibits the activity of phosphatidylinositol 3-kinase within the T cell.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for inhibiting a response by a T cell expressing a CD28 cell surface receptor which binds a costimulatory molecule, comprising contacting the T cell with an agent which acts intracellularly to inhibit production of D-3 phosphoinositides in the T cell, wherein the agent is selected from the group consisting of quercetin and LY294002, and derivatives or analogues thereof.

2. The method of claim 1, wherein the response by the T cell comprises production of at least one lymphokine.

3. The method of claim 2, wherein the lymphokine is interleukin-2.

4. The method of claim 1, wherein the response by the T cell comprises proliferation.

5. The method of claim 1, wherein the costimulatory molecule is B7-1.

6. The method of claim 1, wherein the costimulatory molecule is B7-2.

7. A method for inhibiting a response by a T cell expressing a CD28 cell surface receptor which binds a costimulatory molecule, comprising contacting the T cell with an agent which acts intracellularly to inhibit production of D-3 phosphoinositides in the T cell, and further contacting the T cell with a second agent which inhibits protein tyrosine phosphorylation in the T cell.

8. The method of claim 7, wherein the agent is an inhibitor of phosphatidylinositol 3-kinase.

9. The method of claim 7, wherein the second agent is an inhibitor of a protein tyrosine kinase.

10. The method of claim 9, wherein the inhibitor of a protein tyrosine kinase is herbimycin A or a derivative or analogue thereof.

11. The method of claim 7, wherein the second agent is a tyrosine phosphatase or an activator of a tyrosine phosphatase.

12. The method of claim 11, wherein the tyrosine phosphatase is a cellular tyrosine phosphatase.

13. The method of claim 12, wherein the cellular tyrosine phosphatase is CD45 or Hcph.

14. The method of claim 7, wherein the second agent is a molecule which binds to and activates CD45.

15. The method of claim 14, wherein the second agent is an anti-CD45 antibody, or fragment thereof.

16. The method of claim 8, wherein the inhibitor of phosphatidylinositol 3-kinase is selected from the group consisting of wortmannin, quercetin and LY294002, and derivatives or analogues thereof.

17. The method of claim 7, wherein the response by the T cell comprises production of at least one lymphokine.

18. The method of claim 17, wherein the lymphokine is interleukin-2.

19. The method of claim 7, wherein the response by the T cell comprises proliferation.

* * * * *